United States Patent [19]
Fosberry et al.

[11] Patent Number: 6,111,078
[45] Date of Patent: Aug. 29, 2000

[54] *STAPHYLOCOCCUS AUREUS* RSBU-1

[75] Inventors: Andrew P Fosberry, Linton, United Kingdom; Elizabeth J Lawlor, Malvern; Richard O Nicholas, Collegeville, both of Pa.

[73] Assignees: SmithKline Beecham Corporation, Philadelphia, Pa.; SmithKline Beecham plc, United Kingdom

[21] Appl. No.: 09/340,812

[22] Filed: Jun. 28, 1999

Related U.S. Application Data

[62] Division of application No. 08/938,546, Sep. 26, 1997.
[60] Provisional application No. 60/029,118, Oct. 24, 1996.

[51] Int. Cl.$^7$ .................................................. C07K 14/31
[52] U.S. Cl. ............................................................. 530/350
[58] Field of Search ................................ 530/350; 514/2, 514/12

[56] References Cited

PUBLICATIONS

Wu, et al., "Sigma–B, a Putative Operon Encoding Alternate Sigma Factor of *Staphylococcus aureus* RNA Polymerase: Molecular Cloning and DNA Sequencing" *Journal of Bacteriology*, vol. 178, No. 20, pp. 6036–6042, Oct. 1996.

Kullik, et al., "The Alternative Sigma Factor $\sigma^B$ in *Staphylococcus aureus*: Regulation of the sigB Operon in Response to Growth Phase and Heat Shock", *Arch Microbiol*, vol. 167, pp. 151–159, (1997).

Benjamini, et al., Immunology—A Short Course, Third Edition, Published by Wiley–Liss, (1996).

Davis, et al., "Direct Gene Transfer in Skeletal Muscle: Plasmid DNA–based Immunization Against the Hepatitis B Virus Surface Antigen", *Vaccine*, vol. 12, No. 16, pp. 1503–1509, (1994).

Voelker, et al, "The Yeast Two–Hybrid System Detects Interactions Between *Bacillus subtillis* $\sigma^B$ Regulators", *Journal of Bacteriology*, vol. 178, No. 23, pp. 7020–7023, Dec., 1996.

Sigma Chemical Company catalogue (1993) p. 1761.

Stuart Orkin, M.D. and Arno G. Motulsky, M.D., "Report and Recommendations of the Panel to Assess the NIH Investment in Research on Gene Theraphy" Dec. 7, 1995.

*Primary Examiner*—Robert A. Schwartzman
*Attorney, Agent, or Firm*—Edward G. Gimmi; William T. King; Thomas S. Deibert

[57] ABSTRACT rsbU-1 polypeptides and DNA (RNA) encoding such rsbU-1 and a procedure for producing such polypeptides by recombinant techniques is disclosed. Also disclosed are methods for utilizing such rsbU-1 for the treatment of infection, particularly bacterial infections. Antagonists against such rsbU-1 and their use as a therapeutic to treat infections, particularly bacterial infections are also disclosed. Also disclosed are diagnostic assays for detecting diseases related to the presence of rsbU-1 nucleic acid sequences and the polypeptides in a host. Also disclosed are diagnostic assays for detecting polynucleotides encoding SigB operon and for detecting the polypeptide in a host.

24 Claims, 7 Drawing Sheets

FIGURE 1. rsbU-1cDNA sequence [SEQ ID NO:1]

(1002 nucleotides)

GTGGAAGAATTTAAGCAACATTATAAGGGTTTAATTGATGAAAGTTTAACGTGCCAAGAT
AAAGTAGAATTGATAAAAAAGTGTGAGAAATACACTGACGAAGTGATTCGTAAGGACGTC
TTGCCTGAAGACATTGTCGATATTCACAAAAACTATATATTGACGTTAAACTTAACGCGT
GAAGATGTGTTCAAGACATTAGATGTCTTACAAGAAATCGTTAAAGGCTTTGGTTATAGT
TATCGAGATTATCAAAGATTGGTAGATAAACTTCAAGTTCACGATAAAGAGATAGACTTA
GCTTCTAGCTTACAACCAACAATGCTTAAAACAGATATTCCACAATTTGATAGTATTCAA
ATTGGCGTTATTTCAGTGGCAGCACAAAAAGTAAGTGGAGATTATTTTAATTTAATTGAC
CATAACGATGGCACAATGAGCTTTGCTGTTGCAGATGTCATTGGGAAAGGTATACCAGCT
GCTTTAGCAATGAGTATGATAAAGTTTGGCATGGATTCTTATGGACACTCACAATTACCG
AGTGATGGCTTAAAACGTTTAAATCGTGTTGTTGAAAAGAATATTAATCAAATATGTTC
GTCACAATGTTTTATGGTTTATATGAAGAAATGAACCATTTATTGTATTGTAGTTCAGCT
GGTCATGAGCCTGGATATATTTATCGCGCTGAAAAAGAAGAATTTGAAGAAATTTCAGTT
AGAGGTAGAGTGTTAGGAATCAGTTCACAAACACGATATCAACAACAAGAAATTCCTATA
TACCTTGATGATTTAATTATCATTTTAACGGATGGTGTGACTGAAGCTAGAAATAGTGAA
GGTACCTTTATAGATAAACAAAAACTTTTAGAATATATTAAAAAACATAAACATATGCAC
CCACAAGATATTGTTCAAATTATCTATGAAGCAATTTTAAAGCTTCAAAACCCAAATAAA
AAAGATGATATGACTATTTTGATTATAAAAGAGTAAATTAA

FIGURE 2.  rsbU-1 predicted amino acid sequence [SEQ ID NO:2]

(333 amino acids)

MEEFKQHYKGLIDESLTCQDKVELIKKCEKYTDEVIRKDVLPEDIVDIHKNYILTLNLTR
EDVFKTLDVLQEIVKGFGYSYRDYQRLVDKLQVHDKEIDLASSLQPTMLKTDIPQFDSIQ
IGVISVAAQKVSGDYFNLIDHNDGTMSFAVADVIGKGIPAALAMSMIKFGMDSYGHSQLP
SDGLKRLNRVVEKNINQNMFVTMFYGLYEEMNHLLYCSSAGHEPGYIYRAEKEEFEEISV
RGRVLGISSQTRYQQQEIPIYLDDLIIILTDGVTEARNSEGTFIDKQKLLEYIKKHKHMH
PQDIVQIIYEAILKLQNPNKKDDMTILIIKRVN

FIGURE 3. rsbU-1cDNA sequence [SEQ ID NO:3]

(1020 nucleotides)

GTGAGGAGGCAACTAATCGTGGAAGAATTTAAGCAACATTATAAGGGTTTAATTGATGAA
AGTTTAACGTGCCAAGATAAAGTAGAATTGATAAAAAGTGTGAGAAATACACTGACGAA
GTGATTCGTAAGGACGTCTTGCCTGAAGACATTGTCGATATTCACAAAAACTATATATTG
ACGTTAAACTTAACGCGTGAAGATGTGTTCAAGACATTAGATGTCTTACAAGAAATCGTT
AAAGGCTTTGGTTATAGTTATCGAGATTATCAAAGATTGGTAGATAAACTTCAAGTTCAC
GATAAAGAGATAGACTTAGCTTCTAGCTTACAACCAACAATGCTTAAAACAGATATTCCA
CAATTTGATAGTATTCAAATTGGCGTTATTTCAGTGGCAGCACAAAAGTAAGTGGAGAT
TATTTTAATTTAATTGACCATAACGATGGCACAATGAGCTTTGCTGTTGCAGATGTCATT
GGGAAAGGTATACCAGCTGCTTTAGCAATGAGTATGATAAAGTTTGGCATGGATTCTTAT
GGACACTCACAATTACCGAGTGATGGCTTAAAACGTTTAAATCGTGTTGTTGAAAAGAAT
ATTAATCAAAATATGTTCGTCACAATGTTTTATGGTTTATATGAAGAAATGAACCATTTA
TTGTATTGTAGTTCAGCTGGTCATGAGCCTGGATATATTTATCGCGCTGAAAAAGAAGAA
TTTGAAGAAATTTCAGTTAGAGGTAGAGTGTTAGGAATCAGTTCACAAACACGATATCAA
CAACAAGAAATTCCTATATACCTTGATGATTTAATTATCATTTTAACGGATGGTGTGACT
GAAGCTAGAAATAGTGAAGGTACCTTTATAGATAAACAAAAACTTTTAGAATATATTAAA
AAACATAAACATATGCACCCACAAGATATTGTTCAAATTATCTATGAAGCAATTTTAAAG
CTTCAAAACCCAAATAAAAAGATGATATGACTATTTTGATTATAAAAGAGTAAATTAA

FIGURE 4. rsbU-1 predicted amino acid sequence [SEQ ID NO:4]

(339 amino acids)

MRRQLIVEEFKQHYKGLIDESLTCQDKVELIKKCEKYTDEVIRKDVLPEDIVDIHKNYIL
TLNLTREDVFKTLDVLQEIVKGFGYSYRDYQRLVDKLQVHDKEIDLASSLQPTMLKTDIP
QFDSIQIGVISVAAQKVSGDYFNLIDHNDGTMSFAVADVIGKGIPAALAMSMIKFGMDSY
GHSQLPSDGLKRLNRVVEKNINQNMFVTMFYGLYEEMNHLLYCSSAGHEPGYIYRAEKEE
FEEISVRGRVLGISSQTRYQQQEIPIYLDDLIIILTDGVTEARNSEGTFIDKQKLLEYIK
KHKHMHPQDIVQIIYEAILKLQNPNKKDDMTILIIKRVN

FIGURE 5. Polynucleotide sequence of the sigB putative operon [SEQ ID NO:5]

(3360 nucleotides)

GCAAAATTGCAAACGACCAAAATTGATTAAGTGCAATTAAATAAATGTTAGTAAGTGAAT
CATAATTATCCTTGCTTAAGCATTTGCTTTGTAAGGGAAGTGAGGAGGCAACTAATCGTG
GAAGAATTTAAGCAACATTATAAGGGTTTAATTGATGAAAGTTTAACGTGCCAAGATAAA
GTAGAATTGATAAAAAGTGTGAGAAATACACTGACGAAGTGATTCGTAAGGACGTCTTG
CCTGAAGACATTGTCGATATTCACAAAACTATATATTGACGTTAAACTTAACGCGTGAA
GATGTGTTCAAGACATTAGATGTCTTACAAGAAATCGTTAAAGGCTTTGGTTATAGTTAT
CGAGATTATCAAAGATTGGTAGATAAACTTCAAGTTCACGATAAAGAGATAGACTTAGCT
TCTAGCTTACAACCAACAATGCTTAAAACAGATATTCCACAATTTGATAGTATTCAAATT
GGCGTTATTTCAGTGGCAGCACAAAAAGTAAGTGGAGATTATTTTAATTTAATTGACCAT
AACGATGGCACAATGAGCTTTGCTGTTGCAGATGTCATTGGGAAAGGTATACCAGCTGCT
TTAGCAATGAGTATGATAAAGTTTGGCATGGATTCTTATGGACACTCACAATTACCGAGT
GATGGCTTAAAACGTTTAAATCGTGTTGTTGAAAAGAATATTAATCAAAATATGTTCGTC
ACAATGTTTTATGGTTTATATGAAGAAATGAACCATTTATTGTATTGTAGTTCAGCTGGT
CATGAGCCTGGATATATTTATCGCGCTGAAAAAGAAGAATTTGAAGAAATTTCAGTTAGA
GGTAGAGTGTTAGGAATCAGTTCACAAACACGATATCAACAACAAGAAATTCCTATATAC
CTTGATGATTTAATTATCATTTTAACGGATGGTGTGACTGAAGCTAGAAATAGTGAAGGT
ACCTTTATAGATAAACAAAAACTTTTAGAATATATTAAAAAACATAAACATATGCACCCA
CAAGATATTGTTCAAATTATCTATGAAGCAATTTTAAAGCTTCAAAACCCAAATAAAAAA
GATGATATGACTATTTTGATTATAAAAAGAGTAAATTAATTTAAAAAAGAAGATTAGAAA
TTATTTCGATGGGTATATAATAATTTGAAATATAAATATGGTGGATACAGCGCTTAAAAT
GAAGATAAATATTTTTAATAAGTAGGAGTGTAATGAAATGAATCTTAATATAGAAACAAC
CACTCAAGATAAATTTTACGAAGTTAAAGTCGGTGGAGAATTAGATGTTTATACTGTGCC
TGAATTAGAAGAGGTTTTAACACCTATGAGACAAGATGGAACTCGTGATATTTATGTTAA
TTTAGAAAATGTGAGTTATATGGATTCGACAGGTTTAGGTTTATTCGTAGGTACATTAAA
AGCATTAAACCAAAATGATAAGAACTATACATTTTAGGTGTGTCAGATCGTATCGGTAG
ACTATTTGAATTACTGGTCTTAAGGATTTAATGCATGTTAATGAAGGAACGGAGGTCGA
ATAACATGCAATCTAAAGAAGATTTTATCGAAATGCGCGTGCCAGCATCGGCAGAGTATG

FIGURE 5A.

```
TAAGTTTAATTCGTTTAACACTTTCTGGCGTTTTTTCGAGAGCTGGTGCTACATATGATG
ATATTGAAGATGCCAAGATTGCAGTTAGTGAAGCTGTGACAAATGCAGTTAAACATGCAT
ACAAAGAAAATAACAATGTGGGCATTATTAACATATATTTTGAAATTTTAGAAGATAAAA
TTAAAATTGTTATTTCTGATAAAGGTGACAGTTTTGATTATGAAACAACTAAATCAAAAA
TAGGTCCTTACGATAAAGACGAAAATATAGACTTTTTACGCGAAGGTGGCCTAGGTTTAT
TTTTAATCGAATCTTTAATGGATGAAGTCACAGTATATAAAGAATCTGGTGTGACAATCA
GTATGACTAAGTATATAAAAAAGAGCAGGTGCGAAATAATGGCGAAAGAGTCGAAATCA
GCTAATGAAGTTTCACCTGAGCAAATTAACCAATGGATTAAAGAACACCAAGAAAATAAG
AATACAGATGCACAGGATAAGTTAGTTAAACATTACCAAAAACTAATTGAGTCATTGGCA
TATAAATATTCTAAAGGACAATCACATCACGAAGATTTAGTTCAAGTTGGTATGGTTGGT
TTAATAGGTGCCATAAATAGATTCGATATGTCCTTTGAACGGAAGTTTGAAGCCTTTTTA
GTACCTACTGTAATCGGTGAAATCAAAAGATATCTACGAGATAAAACTTGGAGTGTACAT
GTTCCGAGACGTATTAAAGAAATTGGGCCAAGAATCAAAAAAGTGAGCGATGAACTAACC
GCTGAATTAGAGCGTTCACCTTCTATCAGTGAAATAGCTAATCGATTAGAAGTCTCAGAA
GAAGAAGTGTTAGAAGCAATGGAAATGGGACAAAGTTATAATGCGTTAAGTGTTGATCAT
TCCATTGAAGCTGATAAAGATGGTTCAACTGTTACGCTATTAGATATTATGGGGCAACAA
GATGACCATTATGACTTAACTGAAAAACGTATGATTTTAGAAAAAATATTACCTATATTA
TCTGATCGCGAACGAGAAATCATACAATGTACGTTTATTGAAGGATTGAGTCAAAAGAG
ACAGGTGAGCGTATCGGTTTAAGTCAAATGCATGTATCACGACTTCAGAGAACGGCAATT
AAGAAATTACAAGAAGCAGCACATAAATAGAATTTGCTTATTAATGATACGTTTTATAAT
GAAAAATCCATATAATTATCCCTTGATTATTAAATTGAAATCGAGGGGTATTTTTAATTT
AATTAAGATTTTCGAATTAATACATTATTAACGTAGTTTAATGTGTATCCACATAAATGT
CGCGATATAGTATTAATAATTTAAGTGAAGAAGATATCTAATTGTCGTTTTAAATAGGTG
GATTGCTATTAGAATAAAAAAGTAGTCTTAGATTATGAAATTTAGAAATGATGGTGTGT
CATTTTCAATAATCTTAGTGCGTTTTAAAATATAGTATGACCTAATAATTCGTTTTAAAT
GTTTTGGGAAGTGAAAATTACATTAAGTATCATACCTTAATAGAAGTATTTTAGAATATG
TTAAAATAAATGAGTAAATTTAAGAAAAGTGTGGGTTAAGTAAATGGACAATCAATTGA
TTAATTCAATCATAGAGAAATATCAATTTAGTAAAAACAAATTGAAGCAGTATTAACAC
TGCTAGAAGAAAAAAATACAGTACCATTTATTGCGAGGTATCGAAAAGAGCAAACTGGTG
```

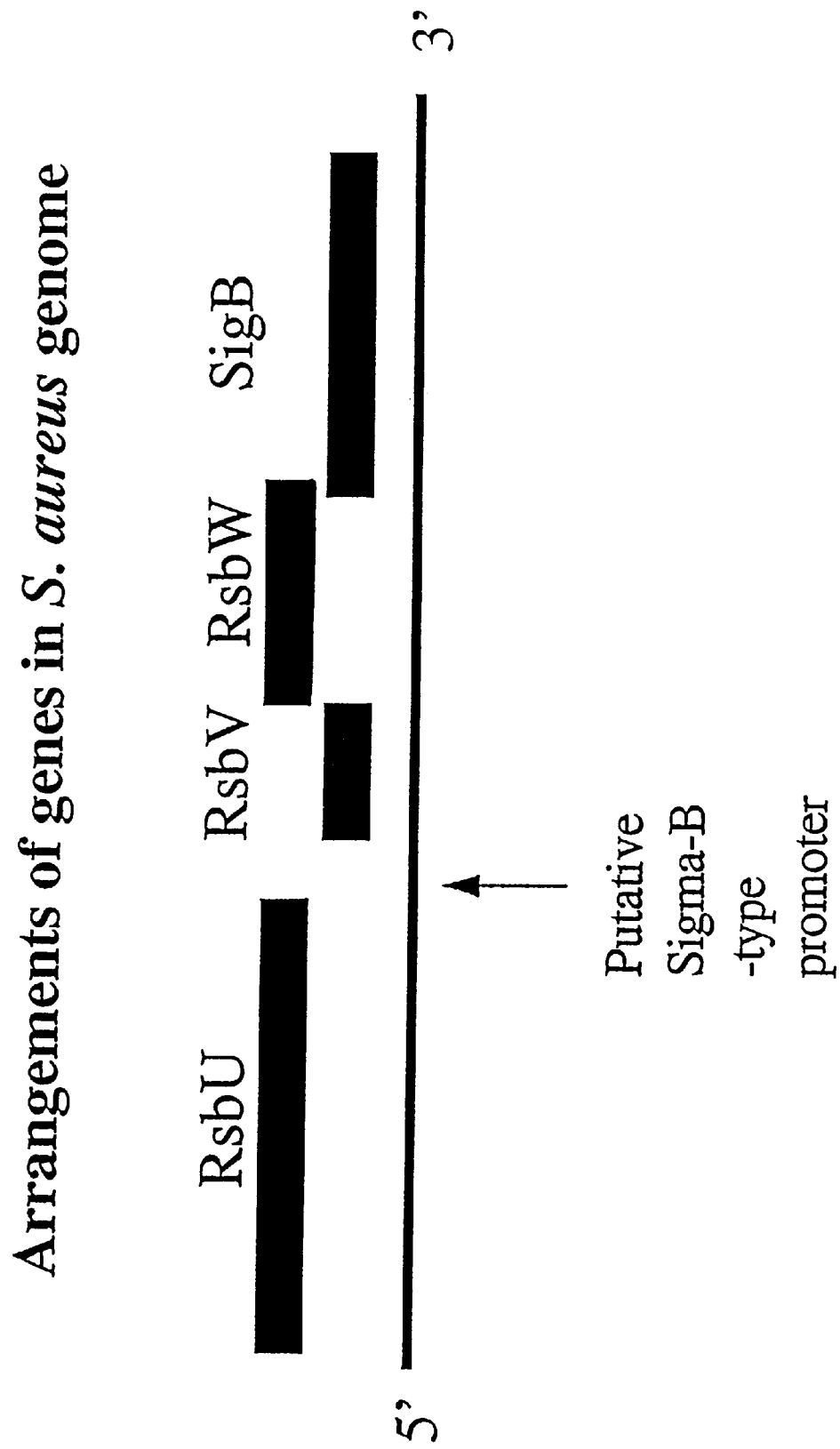
FIGURE 6. sigB putative operon structure

STAPHYLOCOCCUS AUREUS RSBU-1

RELATED APPLICATIONS

This application is a divisional of U.S. application Ser. No. 08/938,546, filed Sep. 26, 1997.

This application claims benefit to U.S. Provisional application 60/029,118 filed Oct. 24, 1996.

FIELD OF THE INVENTION

This invention relates, in part, to newly identified polynucleotides and polypeptides; variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists. In particular, in these and in other regards, the invention relates to polynucleotides and polypeptides of SigB operon, hereinafter referred to as "rsbU-1".

BACKGROUND OF THE INVENTION

Regulation of gene expression in bacteria occurs frequently at the level of transcription. RNA polymerases which transcribe these genes are composed of a multi-subunit core enzyme and an additional protein, or sigma factor, which permits the whole enzyme to recognise promoter elements and initiate transcription at these specific sites. Cells contain multiple sigma factors and their relative levels in the cell provide a fundamental control of gene expression.

Bacillus subtilis has at least 10 different sigma factors [Haldenwang, 1995]. Sigma-B is activated to direct the transcription of a subset of genes when B. subtilis stops exponential growth or is subjected to a number of environmental stresses (eg heat, salt, ethanol and peroxide) [Boylan et al., 1993a,b]. S. aureus, is a pathogen related to Bacillus species. In the host S. aureus cells are exposed to a range of environmental stresses, some analogous to those mentioned above. Furthermore bacterial populations in infection loci are likely to contain slow or non-growing bacteria. Thus an equivalent of sigma-B is likely to play a crucial role in the adaptation of S. aureus to the host environment.

At least four proteins are known to regulate sigma-B. Three (RsbV, RsbW and RsbX) are the products of genes which are co-transcribed with the structural gene for sigma-B (sigB). The fourth (RsbU) lies immediately upstream of the rsbV gene. RsbW binds to sigma-B, blocking sigma-B-dependent transcription. RsbV can form a complex with RsbW and reduce the sequestration of sigma-B by RsbW. Additionally RsbW is able to phosphorylate RsbV to a form which is unable to interact with RsbW [Dufour & Haldenwang, 1995]. RsbU, directly or indirectly, facilitates the RsbV-dependent release of sigma-B from RsbW [Voelker et al., 1995].

Kalman et al. report the similar organisation of the sigB and spoIIA operons encoding alternate sigma factors of Bacillus subtilis. J. Bacteriol. 172, 5575–85 (1980). Further, Wise & Price report that four additional genes in the sigB operon of Bacillus subtilis control activity of the general stress factor sigma-B in response to environmental signals. J. Bacteriol. 177, 123–133(1995).

Clearly, there is a need for factors that may be used to screen compounds for antibiotic activity and which may also be used to determine their roles in pathogenesis of infection, dysfunction and disease. There is a need, therefore, for identification and characterization of such factors which can play a role in preventing, ameliorating or correcting infections, dysfunctions or diseases.

The polypeptide of the present invention has sequence homology to known regulator of a sigma factor.

BACKGROUND REFERENCES

Boylan, S. A., Redfield, A. R. & Price, C. W. (1993a) Transcription factor sigma B of Bacillus subtilis controls a large stationary-phase regulon. Journal of Bacteriology 175, 3957–63.

Boylan, S. A., Redfield, A. R., Brody, M. S. & Price C W. (1993b). Stress-induced activation of the sigma B transcription factor of Bacillus subtilis. Journal of Bacteriology 175, 7931–7.

Dufour, A. & Haldenwang, W. G. (1995). Interactions between a Bacillus subtilis anti-sigma factor (RsbW) and its antagonist (RsbV). Journal of Bacteriology 176, 1813–20.

Haldenwang, W. G. (1995). The sigma factors of Bacillus subtilis. Microbiological Reviews 59, 1–30.

Voelker, U., Dufour, A. & Haldenwang, W. G. (1995). The Bacillus subtilis rsbU gene product is necessary for RsbX-dependent regulation of sigma B. Journal of Bacteriology 177, 114–22.

SUMMARY OF THE INVENTION

Toward these ends, and others, it is an object of the present invention to provide polypeptides, inter alia, that have been identified as novel rsbU-1 by homology between the amino acid sequence set out in FIG. 2 [SEQ ID NO:2] and known amino acid sequences of other proteins such as Bacillus subtilis rsbU.

It is a further object of the invention, moreover, to provide polynucleotides that encode rsbU-1, particularly polynucleotides that encode the polypeptide herein designated rsbU-1.

In a particularly preferred embodiment of this aspect of the invention the polynucleotide comprises the region encoding rsbU-1 in the sequence set out in FIG. 1 [SEQ ID NO:1] and/or FIG. 3 [SEQ ID NO:3], or a fragment, analogue or derivative thereof.

In another particularly preferred embodiment of the present invention there is a novel sigma factor protein from Staphylococcus aureus comprising the amino acid sequence of FIG. 2 [SEQ ID NO:2] and/or Figure [SEQ ID NO:4], or a fragment, analogue or derivative thereof.

In accordance with this aspect of the present invention there is provided an isolated nucleic acid molecule encoding a mature polypeptide expressible by the Staphylococcus aureus polynucleotide contained in NCIMB Deposit No.40771.

In accordance with this aspect of the invention there are provided isolated nucleic acid molecules encoding rsbU-1, particularly Staphylococcus rsbU-1, including mRNAs, cDNAs, genomic DNAs and, in further embodiments of this aspect of the invention include biologically, diagnostically, prophylactically, clinically or therapeutically useful variants, analogs or derivatives thereof, or fragments thereof, including fragments of the variants, analogs and derivatives, and compostions comprising same.

In accordance with another aspect of the present invention, there is provided the use of a polynucleotide of the invention for therapeutic or prophylactic purposes, in particular genetic immunization.

Among the particularly preferred embodiments of this aspect of the invention are naturally occurring allelic variants of rsbU-1 and polypeptides encoded thereby.

In accordance with this aspect of the invention there are provided novel polypeptides of Staphylococcus referred to herein as rsbU-1 as well as biologically, diagnostically, prophylactically, clinically or therapeutically useful fragments, variants and derivatives thereof, variants and derivatives of the fragments, and analogs of the foregoing, and compostions comprising same.

Among the particularly preferred embodiments of this aspect of the invention are variants of rsbU-1 polypeptide encoded by naturally occurring alleles of the rsbU-1 gene.

In a preferred embodiment of this aspect of the invention there are provided methods for producing the aforementioned rsbU-1 polypeptides.

In accordance with yet another aspect of the present invention, there are provided inhibitors to such polypeptides, useful as antibacterial agents, including, for example, antibodies.

In accordance with certain preferred embodiments of this aspect of the invention, there are provided products, compositions and methods, inter alia: assessing rsbU-1 expression; to treat upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis).; assaying genetic variation; and administering a rsbU-1 polypeptide or polynucleotide to an organism to raise an immunological response against a bacteria, especially a Staphylococcus.

In accordance with certain preferred embodiments of this and other aspects of the invention there are polynucleotides that hybridize to rsbU-1 polynucleotide sequences.

In certain additional preferred embodiments of this aspect of the invention there are provided antibodies against rsbU-1 polypeptides.

In accordance with another aspect of the present invention, there are provided rsbU-1 agonists which are also preferably bacteriostatic or bacteriocidal.

In accordance with yet another aspect of the present invention, there are provided rsbU-1 antagonists which are also preferably bacteriostatic or bacteriocidal.

In a further aspect of the invention there are provided compositions comprising a rsbU-1 polynucleotide or a rsbU-1 polypeptide for administration to a cell or to a multicellular organism.

Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the polynucleotide sequence of *Staphylococcus aureus* rsbU-1 [SEQ ID NO:1].

FIG. 2 shows the amino acid sequence of *Staphylococcus aureus* rsbU-1 [SEQ ID NO:2] deduced from the polynucleotide sequence of FIG. 1 [SEQ ID NO:1].

FIG. 3 shows the polynucleotide sequence of *Staphylococcus aureus* rsbU-1 [SEQ ID NO:3].

FIG. 4 shows the amino acid sequence of *Staphylococcus aureus* rsbU-1 [SEQ ID NO:4] deduced from the polynucleotide sequence of FIG. 3 [SEQ ID NO:3].

FIG. 5. shows the polynucleotide sequence of the sigB putative operon [SEQ ID NO:5].

FIG. 6. shows a bar diagram of the sigB putative operon structure including the relative orientations of rsbU-1, rsbV, rsbW and sigB.

GLOSSARY

The following illustrative explanations are provided to facilitate understanding of certain terms used frequently herein, particularly in the Examples. The explanations are provided as a convenience and are not limitative of the invention.

rsbU-1-BINDING MOLECULE, as used herein, refers to molecules or ions which bind or interact specifically with rsbU-1 polypeptides or polynucleotides of the present invention, including, for example enzyme substrates, cell membrane components and classical receptors. Binding between polypeptides of the invention and such molecules, including binding or binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed or transfected, or is capable of transformation or transfection by an exogenous polyncleotide sequence.

IDENTITY or SIMILARITY, as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology,* von Heinje, G., Academic Press, 1987; *Sequence Analysis Primer,* Gribskov, M. and Devereux, J., eds., M Stockton Press, New York, 1991; and Carillo, H., and Lipman, D., SIAM *J. Applied Math.,* 48: 1073 (1988). Methods commonly employed to determine identity or similarity between two sequences include, but are not limited to those disclosed in Carillo, H., and Lipman, D., SLAM *J. Applied Math.,* 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403 (1990)).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS— STRUCTURE AND MOLECULAR PROPERTIES,* 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, E. coli. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination.

DETAILED DESCRIPTION OF THE INVENTION

The present invention relates to novel rsbU-1 polypeptides and polynucleotides, among other things, as described in greater detail below. In particular, the invention relates to polypeptides and polynucleotides of a novel rsbU-1 gene of Staphylococcus aureus, which is related by amino acid sequence homology to in_homo_gensp Bacillus subtilis rsbU polypeptide. The invention relates especially to rsbU-1 having the amino acid sequences set out in FIGS. 1 and 3, and the nucleic acid sequences set out in FIGS. 2, 4 and 5, and to the rsbU-1 nucleotide and amino acid sequences of the DNA in NCIMB Deposit No.40771, which is herein referred to as "the deposited clone" or as the "DNA of the deposited clone." It will be appreciated that the nucleotide and amino acid sequences set out in FIGS. 1 [SEQ ID NO:1] and 2 [SEQ ID NO:2] were obtained by sequencing the DNA of the deposited clone. Hence, the sequence of the deposited clone is controlling as to any discrepancies between it (and the sequence it encodes) and the sequences of FIG. 1 [SEQ ID NO:1] and FIG. 2 [SEQ ID NO:2], or FIG. 3 [SEQ ID NO:3] and FIG. 4 [SEQ ID NO:4].

Polynucleotides

In accordance with one aspect of the present invention, there are provided isolated polynucleotides which encode the rsbU-1 polypeptide having the deduced amino acid sequence of FIG. 2 [SEQ ID NO:2] and/or Figure [SEQ ID NO:4]. Provided are two different GTG initiation codon (methionine) start sites for the gene provided herein.

Using the information provided herein, such as the polynucleotide sequence set out in FIG. 1 [SEQ ID NO:1] and/or FIG. 3 [SEQ ID NO:3] and/or FIG. 5 [SEQ ID NO:5], a polynucleotide of the present invention encoding rsbU-1 polypeptide may be obtained using standard cloning and screening procedures, such as those for cloning and sequencing chromosomal DNA fragments from Staphylococcus aureus WCUH29 cells as starting material, followed by obtaining a full length clone. For example, to obtain a polynucleotide of the invention sequence, such as that sequence given in FIG. 1 [SEQ ID NO:1] and/or FIG. 3 [SEQ ID NO:3] and/or FIG. 5 [SEQ ID NO:5] typically a library of clones of chromosomal DNA of Staphylococcus aureus WCUH29 in E.coli or some other suitable host is probed with a radiolabelled oligonucleotide, preferably a 17-mer or longer, derived from a partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed :using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70). Illustrative of the invention, the polynucleotides set out in FIG. 1 [SEQ ID NO:1], FIG. 3 [SEQ ID NO:3] and FIG. 5 [SEQ ID NO:5] were discovered in a DNA library derived from *Staphylococcus aureus* WCUH29.

RsbU-1 of the invention is structurally related to other proteins of the SigB operon family, as shown by the results of sequencing the DNA encoding rsbU-1 of the deposited clone. The DNA sequences thus obtained are set out in FIG. 1 [SEQ ID NO:1], FIG. 3 [SEQ ID NO:3], and FIG. 5 [SEQ ID NO:5]. It contains an open reading frame encoding a protein of having about the number of amino acid residues set forth in FIG. 2 [SEQ ID NO:2] and FIG. 4 [SEQ ID NO:4] respectively with deduced molecular weights that can be calculated using amino acid residue molecular weight values well known in the art. The protein exhibits greatest homology to *Bacillus subtilis* rsbU protein among known proteins. RsbU-1 of FIG. 2 [SEQ ID NO:2] has about 39.1% identity over its entire length and about 62.1% similarity over its entire length with the amino acid sequence of *Bacillus subtilis* rsbU.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 [SEQ ID NO:1] and/or FIG. 3 [SEQ ID NO:3] and/or FIG. 5 [SEQ ID NO:5]. It also may be a polynucleotide with a different sequence, which, as a result of the redundancy (degeneracy) of the genetic code, encodes the polypeptide of FIG. 2 [SEQ ID NO:2] and/or FIG. 4 [SEQ ID NO:4].

Polynucleotides of the present invention which encode the polypeptide of FIG. 2 [SEQ ID NO:2] and/or FIG. 4 [SEQ ID NO:4] may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci., USA* 86: 821–824 (1989), for instance, hexa-histidine provides for convenient purification of the fusion protein. The HA tag may also be used to create fusion proteins and corresponds to an epitope derived of influenza hemagglutinin protein, which has been described by Wilson et al., *Cell* 37: 767 (1984), for instance. Polynucleotides of the invention also include, but are not limited to, polynucleotides comprising a structural gene and its naturally associated genetic elements.

In accordance with the foregoing, the term "polynucleotide encoding a polypeptide" as used herein encompasses polynucleotides which include a sequence encoding a polypeptide of the present invention, particularly bacterial, and more particularly the *Staphylococcus aureus* rsbU-1 having the amino acid sequence set out in FIG. 2 [SEQ ID NO:2] or FIG. 4 [SEQ ID NO:4]. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 2 [SEQ ID NO:2] and/or FIG. 4 [SEQ ID NO:4]. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of rsbU-1 set out in FIG. 2 [SEQ ID NO:2] and/or FIG. 4 [SEQ ID NO:4]; variants, analogs, derivatives and fragments thereof, and fragments of the variants, analogs and derivatives.

Further particularly preferred in this regard are polynucleotides encoding rsbU-1 variants, analogs, derivatives and fragments, and variants, analogs and derivatives of the fragments, which have the amino acid sequence of rsbU-1 polypeptide of FIG. 2 [SEQ ID NO:2] and/or FIG. 4 [SEQ ID NO:4] in which several, a few, 5 to 10, I to 5, 1 to 3, 2, 1 or no amino acid residues are substituted, deleted or added, in any combination. Especially preferred among these are silent substitutions, additions and deletions, which do not alter the properties and activities of rsbU-1. Also especially preferred in this regard are conservative substitutions. Most highly preferred are polynucleotides encoding polypeptides having the amino acid sequence of FIG. 2 [SEQ ID NO:2] and/or FIG. 4 [SEQ ID NO:4], without substitutions.

Further preferred embodiments of the invention are polynucleotides that are at least 70% identical over their entire length to a polynucleotide encoding rsbU-1 polypeptide having the amino acid sequence set out in FIG. 2 [SEQ ID NO:2] and/or FIG. 4 [SEQ ID NO:4], and polynucleotides which are complementary to such polynucleotides. Alternatively, most highly preferred are polynucleotides that comprise a region that is at least 80% identical over their entire length to a polynucleotide encoding rsbU-1 polypeptide of the *Staphylococcus aureus* DNA of the deposited clone and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments in this respect, moreover, are polynucleotides which encode polypeptides which retain substantially the same biological function or activity as the mature polypeptide encoded by the DNA of FIG. 1 [SEQ ID NO:1] and/or FIG. 3 [SEQ ID NO:3] and/or FIG. 5 [SEQ ID NO:5].

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding rsbU-1 and to isolate cDNA and genomic clones of other genes that have a high sequence similarity to the rsbU-1 gene. Such probes generally will comprise at least 15 bases. Preferably, such probes will have at least 30 bases and may have at least 50 bases. Particularly preferred probes will have at least 30 bases and will have 50 bases or less.

For example, the coding region of the rsbU-1 gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine which members of the library the probe hybridizes to.

The polynucleotides and polypeptides of the present invention may be employed as research reagents and materials for discovery of treatments of and diagnostics for disease, particularly human disease, as further discussed herein relating to polynucleotide assays, inter alia.

The polynucleotides of the invention that are oligonucleotides derived from the sequences of SEQ ID NOS:1 and 2 may be used as PCR primers in the process herein described to determine whether or not the *Staphylococcus aureus* genes identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. § 112.

A deposit containing a *Staphylococcus aureus* rsbU-1 bacterial clone has been deposited with the National Collections of Industrial and Marine Bacteria Ltd. (NCIMB), 23 St. Machar Drive, Aberdeen AB2 1RY, Scotland on Sep. 11, 1995 and assigned NCIMB Deposit No. 40771. The *Staphylococcus aureus* bacterial clone deposit is referred to herein as "the deposited clone" or as "the DNA of the deposited clone."

The deposited material is a bacterial clone that contains the full length rsbU-1 DNA, referred to as "*Staphylococcus areus* WCUH29" upon deposit.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a rsbU-1 polypeptide which has a deduced amino acid sequence of 333 or 339 amino acids in length, as set forth in FIG. 2 [SEQ ID NO:2] and/or FIG. 4 [SEQ ID NO:4] respectively.

The invention also relates to fragments, analogs and derivatives of these polypeptides. The terms "fragment," "derivative" and "analog" when referring to the polypeptide of FIG. 2 [SEQ ID NO:2], means a polypeptide which retains essentially the same biological function or activity as such polypeptide. Thus, an analog includes a proprotein which can be activated by cleavage of the proprotein portion to produce an active mature polypeptide.

The fragment, derivative or analog of the polypeptide of FIG. 2 [SEQ ID NO:2] may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of rsbU-1 set out in FIG. 2 [SEQ ID NO:2], variants, analogs, derivatives and fragments thereof, and variants, analogs and derivatives of the fragments. Alternatively, particularly preferred embodiments of the invention in this regard are polypeptides having the amino acid sequence of the rsbU-1, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the rsbU-1 polypeptide of FIG. 2 [SEQ ID NO:2], in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the rsbU-1. Also especially preferred in this regard are conservative substitutions. Most highly preferred are polypeptides having the amino acid sequence of FIG. 2 [SEQ ID NO:2] without substitutions.

The polypeptides and polynucleotides of the present invention are preferably provided in an isolated form, and preferably are purified to homogeneity.

The polypeptides of the present invention include the polypeptide of FIG. 2 [SEQ ID NO:2] (in particular the mature polypeptide) as well as polypeptides which have at least 70% identity to the polypeptide of FIG. 2 [SEQ ID NO:2], preferably at least 80% identity to the polypeptide of FIG. 2 [SEQ ID NO:2], and more preferably at least 90% similarity (more preferably at least 90% identity) to the polypeptide of FIG. 2 [SEQ ID NO:2] and still more preferably at least 95% similarity (still more preferably at least 95% identity) to the polypeptide of FIG. 2 [SEQ ID NO:2] and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The initial amino acid encoded by the codon "GTG" is indicated in SEQ ID :NO:2 as methionine. However, in one embodiment of the invention, this initial amino acid of a polypeptide of the invention is valine.

Fragments

Also among preferred embodiments of this aspect of the present invention are polypeptides comprising fragments of rsbU-1, most particularly fragments of rsbU-1 having the amino acid set out in FIG. 2 [SEQ ID NO:2], and fragments of variants and derivatives of the rsbU-1 of FIG. 2 [SEQ ID NO:2].

In this regard a fragment is a polypeptide having an amino acid sequence that entirely is the same as part but not all of the amino acid sequence of the aforementioned rsbU-1 polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a rsbU-1 polypeptide of the present comprised within a precursor polypeptide designed for expression in a host and having heterologous pre and pro-polypeptide regions fused to the amino terminus of the rsbU-1 fragment and an additional region fused to the carboxyl terminus of the fragment. Therefore, fragments in one aspect of the meaning intended herein, refers to the portion or portions of a fusion polypeptide or fusion protein derived from rsbU-1.

Representative examples of polypeptide fragments of the invention, include, for example, fragments from amino acid number 1–20, 21–40, 41–60, 61–80, 81–100, and 101–333, and any combination of these 20 amino acid fragments.

In this context "about" herein includes the particularly recited ranges larger or smaller by several, a few, 5, 4, 3, 2 or 1 amino acid at either extreme or at both extremes.

Preferred fragments of the invention include, for example, truncation polypeptides of rsbU-1. Truncation polypeptides include rsbU-1 polypeptides having the amino acid sequence of FIG. 2, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally. Degradation forms of the polypeptides of the invention in a host cell, particularly a Staphylococcus, are also preferred.

Also preferred in this aspect of the invention are fragments characterized by structural or functional attributes of rsbU-1. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of rsbU-1, and combinations of such fragments.

Preferred regions are those that mediate activities of rsbU-1. Most highly preferred in this regard are fragments that have a chemical, biological or other activity of rsbU-1, including those with a similar activity or an improved activity, or with a decreased undesirable activity. Further preferred polypeptide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, host cells, expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989).

Polynucelotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *MOLECULAR CLONING: A LABORATORY MANUAL*, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., *MOLECULAR CLONING, A LABORATORY MANUAL*, 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the *E. coli* lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al., *MOLECULAR CLONING, A LABORATORY MANUAL*, 2nd Ed.; Cold Spring Harbor Laboratory Press, Cold Spring Harbor, N.Y. (1989).

Representative examples of appropriate hosts include bacterial cells, such as streptocooi, staphylococci, *E. coli*, streptomyces and *Salmonella typhimurium* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; ie., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the C- or N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunolglobulin that is useful to solubilize or purify polypeptides. For example, EP-A-O 464 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See, D. Bennett et al., *Journal of Molecular Recognition*, Vol. 8 52–58 (1995) and K. Johanson et al., *The Journal of Biological Chemistry*, Vol. 270, No. 16, pp 9459–9471 (1995).

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression.

RsbU-1 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Polynucleotide assays

This invention is also related to the use of the rsbU-1 polynucleotides to detect complementary polynucleotides such as, for example, as a diagnostic reagent. Detection of rsbU-1 in a eukaryote, particularly a mammal, and especially a human, will provide a diagnostic method for diagnosis of a disease. Eukaryotes (herein also "individual(s)"), particularly mammals, and especially humans, infected with an organism comprising the rsbU-1 gene may be detected at the DNA level by a variety of techniques. Nucleic acids for diagnosis may be obtained from an infected individual's cells and tissues, such as bone, blood, muscle, cartilage, and skin. Genomic DNA may be used directly for detection or may be amplified enzymatically by using PCR (Saiki et al., Nature, 324: 163–166 (1986) prior to analysis. RNA or cDNA may also be used in the same ways. As an example, PCR primers complementary to the nucleic acid encoding rsbU-1 can be used to identify and analyze rsbU-1 presence and/or expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled rsbU-1 RNA or alternatively, radiolabeled rsbU-1 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic characterization based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, e.g., restriction fragment length polymorphisms (RFLP) and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding rsbU-1 can be made using known methods and used to identify and analyze mutations. These primers may be used for amplifying rsbU-1 DNA isolated from a sample derived from an individual. The invention also provides these primers with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be diagnosed.

The invention provides a process for diagnosing, disease, preferably bacterial infections, more preferably Staphylococcus aureus, and most preferably upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis , cutaneous abscesses, cellulitis, wound infection, bacterial myositis) bone and joint (e.g. septic arthritis, osteomyelitis)., comprising determining from a sample derived from an individual a increased level of expression of polynucleotide having the sequence of FIG. 1 [SEQ ID NO:1] and/or FIG. 3 [SEQ ID NO:3] and/or FIG. 5 [SEQ ID NO:5]. Increased expression of rsbU-1 polynucleotide can be measured using any on of the methods well known in the art for the quantation of polynucleotides, such as, for example, PCR, RT-PCR, RNase protection, Northern blotting and other hybridization methods.

Polypeptide assays

The present invention also relates to a diagnostic assays such as quantitative and diagnostic assays for detecting levels of rsbU-1 protein in cells and tissues, including determination of normal and abnormal levels. Thus, for instance, a diagnostic assay in accordance with the invention for detecting over-expression of rsbU-1 protein compared to normal control tissue samples may be used to detect the presence of an infection, for example. Assay techniques that can be used to determine levels of a rsbU-1 protein, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to rsbU-1, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

Antibodies

The polypeptides, their fragments or other derivatives, or analogs thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, such as those in Kohler, G. and Milstein, C., *Nature* 256: 495–497 (1975); Kozbor et al, *Immunology Today* 4: 72 (1983); Cole et al., pg. 77–96 in *MONOCLONAL ANTIBODIES AND CANCER THERAPY*, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilised to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against rsbU-1 may be employed to inhibit and/or treat infections, particularly bacterial infections and especially upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcyocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis).

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognised by certain antibodies which, when raised to the protein or polypeptide according to the present invention, interfere with the immediate physical interaction between pathogen and mammalian host, directly or indirectly. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host, directly or indirectly.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the the protein or polypeptide, or an antigenically or immunologically equivalent polypeptide thereof may be sufficiently antigenic to improve immunogenicity so as to obviate the use of a carrier.

Preferably the antibody or derivative thereof is modified to make it less immunogenic in the individual. For example, if the individual is human the antibody may most preferably be "humanised"; where the complimentarily determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunisation will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers ( Wu et al., J Biol Chem 1989:264,16985), coprecipitation of DNA with calcium phosphate (Benvenisty & Reshef, PNAS,1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

RsbU-1-binding molecules and assays

This invention also provides a method for identification of molecules, such as binding molecules, that bind rsbU-1. Genes encoding proteins that bind rsbU-1, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (1991). Also, a labeled ligand can be photoaffinity linked to a cell extract. Polypeptides of the invention also can be used to assess rsbU-1 binding capacity of rsbU-1-binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be strucural or functional mimetics.

Antagonists and Agonists—assays and molecules

The invention also provides a method of screening compounds to identify those which enhance (agonist) or block (antagonist) the action of rsbU-1 polypeptides or polynucleotides, such as its interaction with rsbU-1-binding molecules.

For example, to screen for agonists or antagoists, a synthetic reaction mix, a cellular compartment, such as a membrane, cell envelope or cell wall, or a preparation of any thereof, may be prepared from a cell that expresses a molecule that binds rsbU-1. The preparation is incubated with labeled rsbU-1 in the absence or the presence of a candidate molecule which may be a rsbU-1 agonist or antagonist. The ability of the candidate molecule to bind the binding molecule is reflected in decreased binding of the labeled ligand. Molecules which bind gratuitously, i.e., without inducing the effects of rsbU-1 on binding the rsbU-1 binding molecule, are most likely to be good antagonists. Molecules that bind well and elicit effects that are the same as or closely related to rsbU-1 are agonists.

RsbU-1-like effects of potential agonists and antagonists may by measured, for instance, by determining activity of a reporter system following interaction of the candidate molecule with a cell or appropriate cell preparation, and comparing the effect with that of rsbU-1 or molecules that elicit the same effects as rsbU-1. Reporter systems that may be useful in this regard include but are not limited to colorimetric labeled substrate converted into product, a reporter gene that is responsive to changes in rsbU-1 activity, and binding assays known in the art.

Another example of an assay for rsbU-1 antagonists is a competitive assay that combines rsbU-1 and a potential antagonist with membrane-bound rsbU-1-binding molecules, recombinant rsbU-1 binding molecules, natural substrates or ligands, or substrate or ligand mimetics, under appropriate conditions for a competitive inhibition assay. RsbU-1 can be labeled, such as by radioactivity or a colorimetric compound, such that the number of rsbU-1 molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing rsbU-1-induced activities, thereby preventing the action of rsbU-1 by excluding rsbU-1 from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules.

Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules).

Preferred potential antagonists include compounds related to and derivatives of rsbU-1.

In a particular aspect the invention provides the use of the polypeptide, polynucleotide or inhibitor of the invention to interfere, directly or indirectly, with the initial physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block sigma factor protein mediated mammalian cell invasion by, for example, initiating phosphorylation of mammalian tyrosine kinases (Rosenshine et al., *Infect. Immun.* 60:2211 (1992); iii) to block bacterial adhesion between mammalian extracellular matrix proteins and bacterial sigma factor proteins which mediate tissue damage; iv) to block the normal progression of pathogenesis in infections initiated other than by the implantation of in-dwelling devices or by other surgical techniques.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists may be employed for instance to inhibit upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis , cutaneous abscesses, cellulitis, wound infection, bacterial myositis) bone and joint (e.g. septic arthritis, osteomyelitis).

Vaccines

Another aspect of the invention relates to a method for inducing an immunological response in an individual, particularly a mammal which comprises inoculating the individual with rsbU-1, or a fragment or variant thereof, adequate to produce antibody to protect said individual from infection, particularly bacterial infection and most particularly Staphylococcus infections. Yet another aspect of the invention relates to a method of inducing immunological response in an individual which comprises, through gene therapy, delivering gene encoding rsbU-1, or a fragment or a variant thereof, for expressing rsbU-1, or a fragment or a variant thereof in vivo in order to induce an immunological response to produce antibody to protect said individual from disease.

A further aspect of the invention relates to an immunological composition which, when introduced into a host capable or having iduced within it an immunological response, induces an immunological response in such host to a rsbU-1 or protein coded therefrom, wherein the composition comprises a recombinant rsbU-1 or protein coded therefrom comprising DNA which codes for and expresses an antigen of said rsbU-1 or protein coded therefrom.

The rsbU-1 or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of *Staphylococcus aureus* infection in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain rsbU-1, it is to be understood that this covers fragments of the naturally occurring protein and similar proteins with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent Staphylococcus wound infections.

Many orthopaedic surgeons consider that humans with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 µg/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of bacteria containing the sigma factor protein.

In order to facilitate understanding of the following example certain frequently occurring methods and/or terms will be described.

EXAMPLES

The present invention is further described by the following examples. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989).

Example 1

Library Production

The polynucleotide having the DNA sequence given in SEQ ID NO:1 was obtained from a library of clones of chromosomal DNA of *Staphylococcus aureus* in *E. coli*. In some cases the sequencing data from two or more clones containing overlapping *Staphylococcus aureus* DNAs was used to construct the contiguous DNA sequence in SEQ ID NO:1. Libraries may be prepared by routine methods, for example: Methods 1 and 2 below.

Total cellular DNA is isolated from *Staphylococcus aureus* WCUH29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2

Total cellular DNA is partially hydrolsed with a combination of four restriction enzymes (RsaI, PalI, AluI and Bsh1235I) and size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

What is claimed is:

1. An isolated protein comprising a polypeptide consisting of SEQ ID NO:2.
2. A composition comprising the isolated protein of claim 1 and a pharmaceutically acceptable carrier.
3. An isolated fusion protein comprising the polypeptide of claim 1 fused to a heterologous amino acid sequence.
4. The isolated protein of claim 1, wherein the isolated protein consists of the polypeptide.
5. A composition comprising the isolated fusion protein of claim 3 and a pharmaceutically acceptable carrier.
6. A composition comprising the isolated protein of claim 4 and a pharmaceutically acceptable carrier.
7. An isolated protein comprising a polypeptide comprising at least 50 consecutive amino acids of SEQ ID NO:2.
8. A composition comprising the isolated protein of claim 7 and a pharmaceutically acceptable carrier.
9. An isolated fusion protein comprising the polypeptide of claim 7 fused to a heterologous amino acid sequence.
10. The isolated protein of claim 7, wherein the isolated protein consists of the polypeptide.
11. A composition comprising the isolated fusion protein of claim 9 and a pharmaceutically acceptable carrier.
12. A composition comprising the isolated protein of claim 10 and a pharmaceutically acceptable carrier.
13. An isolated protein comprising a polypeptide comprising at least 30 consecutive amino acids of SEQ ID NO:2.
14. A composition comprising the isolated protein of claim 13 and a pharmaceutically acceptable carrier.
15. An isolated fusion protein comprising the polypeptide of claim 13 fused to a heterologous amino acid sequence.
16. The isolated protein of claim 13, wherein the isolated protein consists of the polypeptide.
17. A composition comprising the isolated fusion protein of claim 15 and a pharmaceutically acceptable carrier.
18. A composition comprising the isolated protein of claim 16 and a pharmaceutically acceptable carrier.
19. An isolated protein comprising a polypeptide consisting of SEQ ID NO:4.
20. A composition comprising the isolated protein of claim 19 and a pharmaceutically acceptable carrier.
21. An isolated fusion protein comprising the polypeptide of claim 19 fused to a heterologous amino acid sequence.
22. The isolated protein of claim 19, wherein the isolated protein consists of the polypeptide.
23. A composition comprising the isolated fusion protein of claim 21 and a pharmaceutically acceptable carrier.
24. A composition comprising the isolated protein of claim 22 and a pharmaceutically acceptable carrier.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1002 base pairs
      (B) TYPE: nucleic acid
      (C) STRANDEDNESS: double
      (D) TOPOLOGY: linear (xi) SEQUENCE DESCRIPTION: SEQ ID NO:1:

-continued

```
GTGGAAGAAT TTAAGCAACA TTATAAGGGT TTAATTGATG AAAGTTTAAC GTGCCAAGAT      60

AAAGTAGAAT TGATAAAAAA GTGTGAGAAA TACACTGACG AAGTGATTCG TAAGGACGTC     120

TTGCCTGAAG ACATTGTCGA TATTCACAAA AACTATATAT TGACGTTAAA CTTAACGCGT     180

GAAGATGTGT TCAAGACATT AGATGTCTTA CAAGAAATCG TTAAAGGCTT TGGTTATAGT     240

TATCGAGATT ATCAAAGATT GGTAGATAAA CTTCAAGTTC ACGATAAAGA GATAGACTTA     300

GCTTCTAGCT TACAACCAAC AATGCTTAAA ACAGATATTC CACAATTTGA TAGTATTCAA     360

ATTGGCGTTA TTTCAGTGGC AGCACAAAAA GTAAGTGGAG ATTATTTTAA TTTAATTGAC     420

CATAACGATG GCACAATGAG CTTTGCTGTT GCAGATGTCA TTGGGAAAGG TATACCAGCT     480

GCTTTAGCAA TGAGTATGAT AAAGTTTGGC ATGGATTCTT ATGGACACTC ACAATTACCG     540

AGTGATGGCT TAAAACGTTT AAATCGTGTT GTTGAAAAGA ATATTAATCA AAATATGTTC     600

GTCACAATGT TTTATGGTTT ATATGAAGAA ATGAACCATT TATTGTATTG TAGTTCAGCT     660

GGTCATGAGC CTGGATATAT TTATCGCGCT GAAAAGAAG AATTTGAAGA AATTTCAGTT      720

AGAGGTAGAG TGTTAGGAAT CAGTTCACAA ACACGATATC AACAACAAGA AATTCCTATA     780

TACCTTGATG ATTTAATTAT CATTTTAACG GATGGTGTGA CTGAAGCTAG AAATAGTGAA     840

GGTACCTTTA TAGATAAACA AAAACTTTTA GAATATATTA AAAAACATAA ACATATGCAC     900

CCACAAGATA TTGTTCAAAT TATCTATGAA GCAATTTTAA AGCTTCAAAA CCCAAATAAA     960

AAAGATGATA TGACTATTTT GATTATAAAA AGAGTAAATT AA                       1002
```

(2) INFORMATION FOR SEQ ID NO:2:

(i) SEQUENCE CHARACTERISTICS:
        (A) LENGTH: 333 amino acids
        (B) TYPE: amino acid
        (C) STRANDEDNESS: single
        (D) TOPOLOGY: linear (xi) SEQUENCE DESCRIPTION: SEQ ID NO:2:

```
Met Glu Glu Phe Lys Gln His Tyr Lys Gly Leu Ile Asp Glu Ser Leu
  1               5                  10                  15

Thr Cys Gln Asp Lys Val Glu Leu Ile Lys Lys Cys Glu Lys Tyr Thr
                 20                  25                  30

Asp Glu Val Ile Arg Lys Asp Val Leu Pro Glu Asp Ile Val Asp Ile
             35                  40                  45

His Lys Asn Tyr Ile Leu Thr Leu Asn Leu Thr Arg Glu Asp Val Phe
         50                  55                  60

Lys Thr Leu Asp Val Leu Gln Glu Ile Val Lys Gly Phe Gly Tyr Ser
 65                  70                  75                  80

Tyr Arg Asp Tyr Gln Arg Leu Val Asp Lys Leu Gln Val His Asp Lys
                 85                  90                  95

Glu Ile Asp Leu Ala Ser Ser Leu Gln Pro Thr Met Leu Lys Thr Asp
            100                 105                 110

Ile Pro Gln Phe Asp Ser Ile Gln Ile Gly Val Ile Ser Val Ala Ala
        115                 120                 125

Gln Lys Val Ser Gly Asp Tyr Phe Asn Leu Ile Asp His Asn Asp Gly
    130                 135                 140

Thr Met Ser Phe Ala Val Ala Asp Val Ile Gly Lys Gly Ile Pro Ala
145                 150                 155                 160

Ala Leu Ala Met Ser Met Ile Lys Phe Gly Met Asp Ser Tyr Gly His
                165                 170                 175

Ser Gln Leu Pro Ser Asp Gly Leu Lys Arg Leu Asn Arg Val Val Glu
```

```
            180                 185                 190
Lys Asn Ile Asn Gln Asn Met Phe Val Thr Met Phe Tyr Gly Leu Tyr
        195                 200                 205
Glu Glu Met Asn His Leu Leu Tyr Cys Ser Ser Ala Gly His Glu Pro
    210                 215                 220
Gly Tyr Ile Tyr Arg Ala Glu Lys Glu Glu Phe Glu Glu Ile Ser Val
225                 230                 235                 240
Arg Gly Arg Val Leu Gly Ile Ser Ser Gln Thr Arg Tyr Gln Gln Gln
                245                 250                 255
Glu Ile Pro Ile Tyr Leu Asp Asp Leu Ile Ile Leu Thr Asp Gly
            260                 265                 270
Val Thr Glu Ala Arg Asn Ser Glu Gly Thr Phe Ile Asp Lys Gln Lys
        275                 280                 285
Leu Leu Glu Tyr Ile Lys Lys His Lys His Met His Pro Gln Asp Ile
    290                 295                 300
Val Gln Ile Ile Tyr Glu Ala Ile Leu Lys Leu Gln Asn Pro Asn Lys
305                 310                 315                 320
Lys Asp Asp Met Thr Ile Leu Ile Ile Lys Arg Val Asn
                325                 330
```

(2) INFORMATION FOR SEQ ID NO:3:

(i) SEQUENCE CHARACTERISTICS:
        (A) LENGTH: 1020 base pairs
        (B) TYPE: nucleic acid
        (C) STRANDEDNESS: double
        (D) TOPOLOGY: linear (xi) SEQUENCE DESCRIPTION: SEQ ID NO:3:

```
GTGAGGAGGC AACTAATCGT GGAAGAATTT AAGCAACATT ATAAGGGTTT AATTGATGAA    60
AGTTTAACGT GCCAAGATAA AGTAGAATTG ATAAAAAAGT GTGAGAAATA CACTGACGAA   120
GTGATTCGTA AGGACGTCTT GCCTGAAGAC ATTGTCGATA TTCACAAAAA CTATATATTG   180
ACGTTAAACT TAACGCGTGA AGATGTGTTC AAGACATTAG ATGTCTTACA AGAAATCGTT   240
AAAGGCTTTG GTTATAGTTA TCGAGATTAT CAAAGATTGG TAGATAAACT TCAAGTTCAC   300
GATAAAGAGA TAGACTTAGC TTCTAGCTTA CAACCAACAA TGCTTAAAAC AGATATTCCA   360
CAATTTGATA GTATTCAAAT TGGCGTTATT TCAGTGGCAG CACAAAAAGT AAGTGGAGAT   420
TATTTTAATT TAATTGACCA TAACGATGGC ACAATGAGCT TTGCTGTTGC AGATGTCATT   480
GGGAAAGGTA TACCAGCTGC TTTAGCAATG AGTATGATAA AGTTTGGCAT GGATTCTTAT   540
GGACACTCAC AATTACCGAG TGATGGCTTA AAACGTTTAA ATCGTGTTGT TGAAAAGAAT   600
ATTAATCAAA ATATGTTCGT CACAATGTTT TATGGTTTAT ATGAAGAAAT GAACCATTTA   660
TTGTATTGTA GTTCAGCTGG TCATGAGCCT GGATATATTT ATCGCGCTGA AAAAGAAGAA   720
TTTGAAGAAA TTTCAGTTAG AGGTAGAGTG TTAGGAATCA GTTCACAAAC ACGATATCAA   780
CAACAAGAAA TTCCTATATA CCTTGATGAT TTAATTATCA TTTTAACGGA TGGTGTGACT   840
GAAGCTAGAA ATAGTGAAGG TACCTTTATA GATAAACAAA AACTTTTAGA ATATATTAAA   900
AAACATAAAC ATATGCACCC ACAAGATATT GTTCAAATTA TCTATGAAGC AATTTTAAAG   960
CTTCAAAACC CAAATAAAAA AGATGATATG ACTATTTTGA TTATAAAAAG AGTAAATTAA  1020
```

(2) INFORMATION FOR SEQ ID NO:4:

(i) SEQUENCE CHARACTERISTICS:
        (A) LENGTH: 339 amino acids (B) TYPE: amino acid
        (C) STRANDEDNESS: single
        (D) TOPOLOGY: linear (xi) SEQUENCE DESCRIPTION: SEQ ID NO:4:

Met Arg Arg Gln Leu Ile Val Glu Phe Lys Gln His Tyr Lys Gly
1               5                   10                  15

Leu Ile Asp Glu Ser Leu Thr Cys Gln Asp Lys Val Glu Leu Ile Lys
            20                  25                  30

Lys Cys Glu Lys Tyr Thr Asp Glu Val Ile Arg Lys Asp Val Leu Pro
        35                  40                  45

Glu Asp Ile Val Asp Ile His Lys Asn Tyr Ile Leu Thr Leu Asn Leu
    50                  55                  60

Thr Arg Glu Asp Val Phe Lys Thr Leu Asp Val Leu Gln Glu Ile Val
65                  70                  75                  80

Lys Gly Phe Gly Tyr Ser Tyr Arg Asp Tyr Gln Arg Leu Val Asp Lys
                85                  90                  95

Leu Gln Val His Asp Lys Glu Ile Asp Leu Ala Ser Ser Leu Gln Pro
            100                 105                 110

Thr Met Leu Lys Thr Asp Ile Pro Gln Phe Asp Ser Ile Gln Ile Gly
        115                 120                 125

Val Ile Ser Val Ala Ala Gln Lys Val Ser Gly Asp Tyr Phe Asn Leu
    130                 135                 140

Ile Asp His Asn Asp Gly Thr Met Ser Phe Ala Val Ala Asp Val Ile
145                 150                 155                 160

Gly Lys Gly Ile Pro Ala Ala Leu Ala Met Ser Met Ile Lys Phe Gly
                165                 170                 175

Met Asp Ser Tyr Gly His Ser Gln Leu Pro Ser Asp Gly Leu Lys Arg
            180                 185                 190

Leu Asn Arg Val Val Glu Lys Asn Ile Asn Gln Asn Met Phe Val Thr
        195                 200                 205

Met Phe Tyr Gly Leu Tyr Glu Glu Met Asn His Leu Leu Tyr Cys Ser
    210                 215                 220

Ser Ala Gly His Glu Pro Gly Tyr Ile Tyr Arg Ala Glu Lys Glu Glu
225                 230                 235                 240

Phe Glu Glu Ile Ser Val Arg Gly Arg Val Leu Gly Ile Ser Ser Gln
                245                 250                 255

Thr Arg Tyr Gln Gln Gln Glu Ile Pro Ile Tyr Leu Asp Asp Leu Ile
            260                 265                 270

Ile Ile Leu Thr Asp Gly Val Thr Glu Ala Arg Asn Ser Glu Gly Thr
        275                 280                 285

Phe Ile Asp Lys Gln Lys Leu Leu Glu Tyr Ile Lys Lys His Lys His
    290                 295                 300

Met His Pro Gln Asp Ile Val Gln Ile Ile Tyr Glu Ala Ile Leu Lys
305                 310                 315                 320

Leu Gln Asn Pro Asn Lys Lys Asp Asp Met Thr Ile Leu Ile Ile Lys
                325                 330                 335

Arg Val Asn (2) INFORMATION FOR SEQ ID NO:5:

(i) SEQUENCE CHARACTERISTICS:
        (A) LENGTH: 3360 base pairs
        (B) TYPE: nucleic acid
        (C) STRANDEDNESS: double
        (D) TOPOLOGY: linear (xi) SEQUENCE DESCRIPTION: SEQ ID NO:5:

```
GCAAAATTGC AAACGACCAA AATTGATTAA GTGCAATTAA ATAAATGTTA GTAAGTGAAT      60
CATAATTATC CTTGCTTAAG CATTTGCTTT GTAAGGGAAG TGAGGAGGCA ACTAATCGTG     120
GAAGAATTTA AGCAACATTA TAAGGGTTTA ATTGATGAAA GTTTAACGTG CCAAGATAAA     180
GTAGAATTGA TAAAAAAGTG TGAGAAATAC ACTGACGAAG TGATTCGTAA GGACGTCTTG     240
CCTGAAGACA TTGTCGATAT TCACAAAAAC TATATATTGA CGTTAAACTT AACGCGTGAA     300
GATGTGTTCA AGACATTAGA TGTCTTACAA GAAATCGTTA AAGGCTTTGG TTATAGTTAT     360
CGAGATTATC AAAGATTGGT AGATAAACTT CAAGTTCACG ATAAAGAGAT AGACTTAGCT     420
TCTAGCTTAC AACCAACAAT GCTTAAAACA GATATTCCAC AATTTGATAG TATTCAAATT     480
GGCGTTATTT CAGTGGCAGC ACAAAAAGTA AGTGGAGATT ATTTTAATTT AATTGACCAT     540
AACGATGGCA CAATGAGCTT TGCTGTTGCA GATGTCATTG GGAAAGGTAT ACCAGCTGCT     600
TTAGCAATGA GTATGATAAA GTTTGGCATG GATTCTTATG ACACTCACA ATTACCGAGT      660
GATGGCTTAA AACGTTTAAA TCGTGTTGTT GAAAAGAATA TTAATCAAAA TATGTTCGTC     720
ACAATGTTTT ATGGTTTATA TGAAGAAATG AACCATTTAT TGTATTGTAG TTCAGCTGGT     780
CATGAGCCTG GATATATTTA TCGCGCTGAA AAAGAAGAAT TTGAAGAAAT TTCAGTTAGA     840
GGTAGAGTGT TAGGAATCAG TTCACAAACA CGATATCAAC AACAAGAAAT TCCTATATAC     900
CTTGATGATT TAATTATCAT TTTAACGGAT GGTGTGACTG AAGCTAGAAA TAGTGAAGGT     960
ACCTTTATAG ATAAACAAAA ACTTTTAGAA TATATTAAAA AACATAAACA TATGCACCCA    1020
CAAGATATTG TTCAAATTAT CTATGAAGCA ATTTTAAAGC TTCAAAACCC AAATAAAAAA    1080
GATGATATGA CTATTTTGAT TATAAAAAGA GTAAATTAAT TTAAAAAAGA AGATTAGAAA    1140
TTATTTCGAT GGGTATATAA TAATTTGAAA TATAAATATG GTGGATACAG CGCTTAAAAT    1200
GAAGATAAAT ATTTTTAATA AGTAGGAGTG TAATGAAATG AATCTTAATA TAGAAACAAC    1260
CACTCAAGAT AAATTTTACG AAGTTAAAGT CGGTGGAGAA TTAGATGTTT ATACTGTGCC    1320
TGAATTAGAA GAGGTTTTAA CACCTATGAG ACAAGATGGA ACTCGTGATA TTTATGTTAA    1380
TTTAGAAAAT GTGAGTTATA TGGATTCGAC AGGTTTAGGT TTATTCGTAG GTACATTAAA    1440
AGCATTAAAC CAAAATGATA AAGAACTATA CATTTTAGGT GTGTCAGATC GTATCGGTAG    1500
ACTATTTGAA ATTACTGGTC TTAAGGATTT AATGCATGTT AATGAAGGAA CGGAGGTCGA    1560
ATAACATGCA ATCTAAAGAA GATTTTATCG AAATGCGCGT GCCAGCATCG GCAGAGTATG    1620
TAAGTTTAAT TCGTTTAACA CTTTCTGGCG TTTTTTCGAG AGCTGGTGCT ACATATGATG    1680
ATATTGAAGA TGCCAAGATT GCAGTTAGTG AAGCTGTGAC AAATGCAGTT AAACATGCAT    1740
ACAAAGAAAA TAACAATGTG GGCATTATTA ACATATATTT TGAAATTTTA AAGATAAAA     1800
TTAAAATTGT TATTTCTGAT AAAGGTGACA GTTTTGATTA TGAAACAACT AAATCAAAAA    1860
TAGGTCCTTA CGATAAAGAC GAAAATATAG ACTTTTTACG CGAAGGTGGC CTAGGTTTAT    1920
TTTTAATCGA ATCTTTAATG GATGAAGTCA CAGTATATAA AGAATCTGGT GTGACAATCA    1980
GTATGACTAA GTATATAAAA AAAGAGCAGG TGCGAAATAA TGGCGAAAGA GTCGAAATCA    2040
GCTAATGAAG TTTCACCTGA GCAAATTAAC CAATGGATTA AGAACACCA AGAAAATAAG     2100
AATACAGATG CACAGGATAA GTTAGTTAAA CATTACCAAA ACTAATTGA GTCATTGGCA     2160
TATAAATATT CTAAAGGACA ATCACATCAC GAAGATTTAG TTCAAGTTGG TATGGTTGGT    2220
TTAATAGGTG CCATAAATAG ATTCGATATG TCCTTTGAAC GGAAGTTTGA AGCCTTTTTA    2280
```

```
                                          -continued
GTACCTACTG TAATCGGTGA AATCAAAAGA TATCTACGAG ATAAAACTTG GAGTGTACAT    2340

GTTCCGAGAC GTATTAAAGA AATTGGGCCA AGAATCAAAA AAGTGAGCGA TGAACTAACC    2400

GCTGAATTAG AGCGTTCACC TTCTATCAGT GAAATAGCTA ATCGATTAGA AGTCTCAGAA    2460

GAAGAAGTGT TAGAAGCAAT GGAAATGGGA CAAAGTTATA ATGCGTTAAG TGTTGATCAT    2520

TCCATTGAAG CTGATAAAGA TGGTTCAACT GTTACGCTAT TAGATATTAT GGGGCAACAA    2580

GATGACCATT ATGACTTAAC TGAAAAACGT ATGATTTTAG AAAAAATATT ACCTATATTA    2640

TCTGATCGCG AACGAGAAAT CATACAATGT ACGTTTATTG AAGGATTGAG TCAAAAAGAG    2700

ACAGGTGAGC GTATCGGTTT AAGTCAAATG CATGTATCAC GACTTCAGAG AACGGCAATT    2760

AAGAAATTAC AAGAAGCAGC ACATAAATAG AATTTGCTTA TTAATGATAC GTTTTATAAT    2820

GAAAAATCCA TATAATTATC CCTTGATTAT TAAATTGAAA TCGAGGGGTA TTTTTAATTT    2880

AATTAAGATT TTCGAATTAA TACATTATTA ACGTAGTTTA ATGTGTATCC ACATAAATGT    2940

CGCGATATAG TATTAATAAT TTAAGTGAAG AAGATATCTA ATTGTCGTTT TAAATAGGTG    3000

GATTGCTATT AGAATAAAAA AAGTAGTCTT AGATTATGAA ATTTAGAAAT GATGGTGTGT    3060

CATTTTCAAT AATCTTAGTG CGTTTTAAAA TATAGTATGA CCTAATAATT CGTTTTAAAT    3120

GTTTTGGGAA GTGAAAATTA CATTAAGTAT CATACCTTAA TAGAAGTATT TTAGAATATG    3180

TTAAAATAAA TGAGTAAATT TAAGAAAAAG TGTGGGTTAA GTAAATGGAC AATCAATTGA    3240

TTAATTCAAT CATAGAGAAA TATCAATTTA GTAAAAAACA AATTGAAGCA GTATTAACAC    3300

TGCTAGAAGA AAAAAATACA GTACCATTTA TTGCGAGGTA TCGAAAAGAG CAAACTGGTG    3360
```